United States Patent
Hu (10) Patent No.: US 6,547,812 B1
(45) Date of Patent: Apr. 15, 2003

(54) RADIATION THERAPY USING A RADIOACTIVE IMPLANTABLE DEVICE AND A RADIOSENSITIZER AGENT

(75) Inventor: Ty T. Hu, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 77 days.

(21) Appl. No.: 09/750,674

(22) Filed: Dec. 29, 2000

(51) Int. Cl.[7] .................................................. A61F 2/06
(52) U.S. Cl. ..................... 623/1.11; 623/1.34; 623/1.43; 623/1.45
(58) Field of Search ....................... 623/1.13, 1.14–1.17, 623/1.44–1.46; 427/5, 6

(56) References Cited

U.S. PATENT DOCUMENTS

| | | | |
|---|---|---|---|
| 4,315,002 A | | 2/1982 | Maurer |
| 5,059,166 A | | 10/1991 | Fischell et al. |
| 5,080,455 A | | 1/1992 | King et al. |
| 5,096,694 A | | 3/1992 | Quivy et al. |
| 5,176,617 A | | 1/1993 | Fischell et al. |
| 5,213,561 A | | 5/1993 | Weinstein et al. |
| 5,342,283 A | * | 8/1994 | Good ............................ 600/8 |
| 5,366,504 A | | 11/1994 | Andersen et al. |
| 5,464,450 A | | 11/1995 | Buscemi et al. |
| 5,500,013 A | | 3/1996 | Buscemi et al. |
| 5,551,954 A | | 9/1996 | Buscemi et al. |
| 5,591,227 A | | 1/1997 | Dinh et al. |
| 5,599,352 A | | 2/1997 | Dinh et al. |
| 5,607,442 A | | 3/1997 | Fischell et al. |
| 5,622,946 A | | 4/1997 | Sessler et al. |
| 5,641,764 A | * | 6/1997 | Martin et al. .................. 514/80 |
| 5,697,967 A | | 12/1997 | Dinh et al. |

(List continued on next page.)

FOREIGN PATENT DOCUMENTS

| | | |
|---|---|---|
| WO | WO 98/23228 | 6/1998 |

OTHER PUBLICATIONS

Fischell, Tim A. et al.., "Low–Dose, Beta Particle Emission From 'Stent' Wire Results in Complete, Localized Inhibition of Smooth Muscle Cell Proliferation", Circulation vol. 90 No. 6, 1994.

Hehrlien, Christoph et al.., "Low–Dose Radioactive Endovascular Stents Prevent Smooth Muscle Cell Proliferation and Neointimal Hyperplasia in Rabbits", Circulation vol. 92 No. 6, 1995.

Hehrlien, Christoph et al.., "Radioactive Stents", Abstract 22.

Fischell, Robert E. et al.., "The Radioisotope Stent: Conception And Implementation", Abstract 37.

Popowski, Youri et al.., "Radioactive Wire In a Self–Centering Catheter System", Abstract 38.

Martin, Louis G., "Radiation For Peripheral Applications: Technical Aspects", Abstract 27.

Li, Alexander N. et al., "A Novel Brachyehtapy Source For Treatment of Coronary Artery Restenosis", Abstract 24.

Teirstein, Paul S. et al., "Catheter–Based Radiation Therapy To Inhibit Restenosis Following Coronary Stenting", Abstract 31.

*Primary Examiner*—Corrine McDermott
*Assistant Examiner*—Hieu Phan
(74) *Attorney, Agent, or Firm*—Blakely, Sokoloff, Taylor & Zafman LLP (57) ABSTRACT

A method and apparatus for inhibiting vascular restenosis using a radioactive implantable medical device and a radiosensitizer agent. In one embodiment, the method of the invention includes implanting a medical device at a blood vessel site that has undergone a procedure to open a stenosed region within a blood vessel. The medical device contains a radioisotope to emit a radioactivity to a tissue mass at the blood vessel site. The method further includes delivering a radiosensitizer agent to the tissue mass at the blood vessel site. The radiosensitizer agent increases a therapeutic response of the tissue mass to the radioactivity emitted by the radioisotope.

57 Claims, 4 Drawing Sheets

U.S. PATENT DOCUMENTS

| | | |
|---|---|---|
| 5,725,572 A | 3/1998 | Lam et al. |
| 5,728,042 A | 3/1998 | Schwager |
| 5,730,698 A | 3/1998 | Fischell et al. |
| 5,765,418 A | 6/1998 | Rosenberg |
| 5,769,883 A | 6/1998 | Buscemi et al. |
| 5,824,056 A | 10/1998 | Rosenberg |
| 5,837,313 A | 11/1998 | Ding et al. |
| 5,857,998 A | 1/1999 | Barry |
| 5,871,436 A | 2/1999 | Eury |
| 5,871,437 A | 2/1999 | Alt |
| 5,873,904 A | 2/1999 | Ragheb et al. |
| 5,888,997 A | 3/1999 | Sessler et al. |
| 5,893,852 A | 4/1999 | Morales |
| 5,906,573 A | 5/1999 | Aretz |
| 5,972,027 A | 10/1999 | Johnson |
| 5,985,266 A | 11/1999 | Link, Jr. et al. |
| 6,010,445 A | 1/2000 | Armini et al. |
| 6,022,374 A | 2/2000 | Imran |
| 6,048,362 A | 4/2000 | Berg |
| 6,071,305 A | 6/2000 | Brown et al. |
| 6,093,199 A | 7/2000 | Brown et al. |
| 6,099,455 A | 8/2000 | Columbo et al. |
| 6,099,457 A * | 8/2000 | Good .......................... 600/8 |
| 6,296,603 B1 * | 10/2001 | Trunlund et al. .............. 600/3 |

\* cited by examiner

RADIATION THERAPY USING A RADIOACTIVE IMPLANTABLE DEVICE AND A RADIOSENSITIZER AGENT

BACKGROUND OF THE INVENTION

1. Field of the Invention

The present invention relates generally to intravascular radiation therapy. More specifically, the present invention relates to radiation therapy for inhibition of vascular restenosis using an intravascular radioactive implantable device and a radiosensitizer agent.

2. Description of Related Art

In a typical balloon PTCA procedure, a catheter is inserted into the cardiovascular system via a femoral artery under local anesthesia. A pre-shaped guiding catheter is positioned in the coronary artery, and a dilatation catheter having a distensible balloon portion is advanced through the guiding catheter into the branches of the coronary artery until the balloon portion traverses or crosses a stenotic lesion. The balloon portion is then inflated with an inflation medium to compress the stenotic lesion in a direction generally perpendicular to the wall of the artery, thus dilating the lumen of the artery.

Patients treated by PTCA procedures, however, suffer from an incidence of restenosis i.e., at or near the original site of the stenosis in which the coronary vessel collapses or becomes obstructed by extensive tissue growth intimal hyperplasia. When restenosis occurs, a second angioplasty procedure or even bypass surgery may be required, depending upon the degree of restenosis.

Clinical studies have indicated that anti-proliferative drug therapy or intravascular radiation after balloon angioplasty or an atherectomy procedure can prevent or reduce the rate of restenosis caused by intimal hyperplasia. In order to reduce or prevent restenosis, anti-proliferative agents or intravascular radiotherapy or radiation therapy is generally given at high toxicity or very high doses. For many patients, however, receiving high doses of radiation in a short amount of time could have long-term negative consequences. In addition, treating patients with high dose radiotherapy e.g., external radiation beam or brachytherapy may only be performed in specially built facilities and requires strict adherence to numerous radiation safety regulations, ultimately adding to the cost of the procedure.

To overcome the disadvantages associated with high-dose radiotherapy procedures, medical practitioners have increasingly relied on low-dose intravascular radiation therapy i.e., radiotherapy for treatment of restenosis. One approach of performing low-dose intravascular radiotherapy involves inserting a flexible catheter into the cardiovascular system of a patient and then advancing the catheter to the region of the vessel that has been subjected to the angioplasty procedure. A radiation source or a treatment catheter having a radiation source inside is then advanced through the flexible catheter so that the radiation source reaches the stenosed vascular site and can deliver an effective dose of radiation. After the radiation treatment is completed, the catheter and radiation source are removed.

Another approach of performing intravascular radiotherapy to prevent or reduce the rate of restenosis involves the use of an implantable radioactive device, such as a radioactive stent, with either beta-emitting or gamma-emitting radioisotopes. Intravascular implantation of a radioactive stent generally involves advancing the stent on a balloon catheter or a similar device to the designated vessel site and deploying the stent by inflating the balloon which then expands the stent radially against the wall of the vessel. Once the stent is properly positioned and secured in place at the vessel site, the balloon is deflated and the catheter is removed from the patient.

The use of implantable radioactive stents, however, is not without some disadvantages. Preliminary clinical studies indicate that although a radioactive stent will eliminate the proliferation of smooth muscle cells e.g., following a PTCA or stent procedure inside the vessel area of the stent, the use of implantable radioactive stents may increase the restenosis rate in the area of the vessel immediately beyond the longitudinal ends of the stent e.g., "stent edge effects". The smooth muscle cell growth immediately beyond the implanted radioactive stent tends to resemble a shape not unlike the ends of a candy wrapper. Hence, some in the medical community generally apply the term "candy wrapper" to this phenomenon.

Although the precise cause of the "stent edge effects" is currently unknown, some in the medical community have suggested that these effects may be caused by the use of a radioactive stent having a length smaller that the actual length of the vessel site that was treated during angioplasty coupled with the failure or inability to properly treat the entire vessel lesion site with sufficient amounts of radiation.

Some techniques for minimizing thrombus formation, inflammation and restenosis of the vessel have been focused on improving the design of the radioactive stent and/or its delivering device e.g., catheter balloon to permit for a smoother and more precise implantation of the stent at the vessel treatment site. Other techniques rely on coating the surface of the radioactive stent with various types of drugs or substances to inhibit the proliferation of smooth muscle cells. Still yet other techniques use "hot ends" and "uneven" dose loading along the stent when trying to eliminate the "candy wrapper" effects and/or to increase the effective dose rate range for radioactive implantable stents. None of the these techniques, however, are effective in preventing or minimizing the "stent edge effects" or "candy wrapper" effects associated with the use of radioactive stents.

Given the significant clinical benefits associated with the use of implantable radioactive stents to prevent or reduce vascular restenosis, it is useful to develop a method that will eliminate one of the possible mechanisms causing the "stent edge effects" or "candy wrapper" effects: the failure or inability to properly treat the entire vessel lesion site with sufficient amounts of radiation. To this end, it is advantageous to develop a method that will enable the effective dose range of the radiation to extend as far as possible outside the radioactive stent and thus allow the injured vessel site beyond the length of the stent to be properly treated. It is also helpful that this method be made as minimally invasive as possible and without any significant adverse health effects to the patient. Furthermore, it is useful that this method be simple to implement and be as safe as possible to patients and health care professionals.

SUMMARY OF THE INVENTION

A method for inhibiting vascular restenosis is described. In one embodiment, the method includes implanting a medical device at a blood vessel site that has undergone a procedure to open a stenosed region within a blood vessel. The medical device contains a radioisotope to emit a radioactivity to a tissue mass at the blood vessel site. The method further includes delivering a radiosensitizer agent to the tissue mass at the blood vessel site. The radiosensitizer agent increases a therapeutic response of the tissue mass to the radioactivity emitted by the radioisotope.

BRIEF DESCRIPTION OF THE DRAWINGS

The present invention is illustrated by way of example and not limitation in the accompanying figures.

DETAILED DESCRIPTION OF THE INVENTION

A method and apparatus for inhibiting vascular restenosis using an intravascular radioactive implantable medical device and a radiosensitizer agent are described.

In the following detailed description, numerous specific details are set forth in order to provide a more thorough understanding of the present invention. However, it will be apparent to those skilled in the art to which this invention pertains that the present invention may be practiced without these specific details. In other instances, well-known devices, methods, procedures, and individual components have not been described in detail so as not to obscure aspects of the present invention.

The method of this invention utilizes intravascular implantation of a radioactive medical device, such as a radioactive stent, and a radiosensitizer agent to prevent or minimize vascular restenosis.

Figure 1:
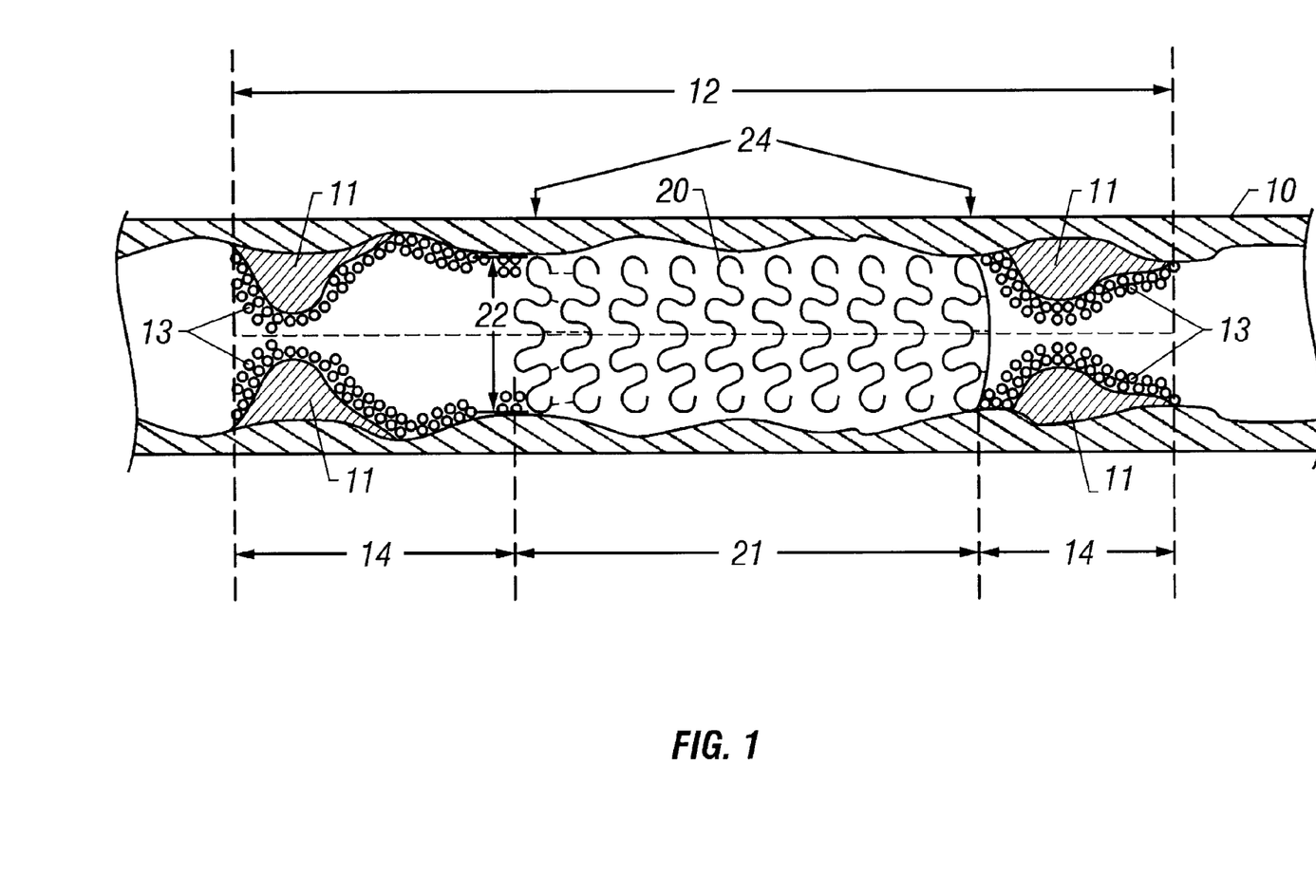
FIG. 1 illustrates an embodiment of an implantable radioactive medical device, such as a stent, positioned at a site within a body vessel to inhibit the "candy wrapper" restenosis.

FIG. 1 illustrates an embodiment of a radiation therapy system 1 of this invention. The radiation therapy system 1 generally includes an implantable medical device 20 and a radiosensitizer agent 13. The implantable medical device 20 contains a radioisotope to emit a radioactivity to at least a tissue mass 11 at a blood vessel site 10 that has undergone a procedure to open a stenosed region within a blood vessel. The radiosensitizer agent 13 increases the therapeutic response of the tissue mass 11 to the radioactivity emitted by the radioisotope. During radiation therapy, the radioactive implantable device 20 and the radiosensitizer agent 13 are disposed at the blood vessel site.

Continuing with reference to FIG. 1, an embodiment of an implantable radioactive medical device 20 for practicing this invention, such as a radioactive stent, positioned inside a body vessel, for example a blood vessel 10, is illustrated. When deployed, the implantable radioactive medical device 20, e.g. stent 20, has a length 21 and an expanded diameter 22. Low-dose implantable radioactive medical devices, such as radioactive stents 20, generally employ beta-emitting radioisotopes, such as Phosphorus-32, or low penetration gamma-emitting radioisotopes, such as Palladium 103. Given the very short travel length of beta particles or low energy gamma rays, the therapeutic radiation dose administered to the body vessel drops significantly 2–4 mm from the longitudinal ends 24 of radioactive stent 20.

The use of implantable radioactive medical devices, e.g. radioactive stents, may cause an increase in the restenosis rate in the areas 14 of the vessel 10 that are immediately outside the longitudinal ends 24 of the stent 20. The "candy wrapper"-shape restenosis, shown as item 11 in FIG. 1, may be caused by a failure or inability to treat the entire vessel lesion site 12 with sufficient amounts of radiation. One of the challenges for intravascular radioactive medical device, e.g. stent, implantations is to achieve optimal therapeutic radiation dosimetry in the vessel lesion area along the length 21 of medical device 20, e.g. stent 20, as well as in the areas 14 immediately outside the medical device 20 since vessel areas 14 just beyond the longitudinal ends 24 of the stent 20 are most susceptible to damage from medical device, e.g. stent, deployment/implantation. Increasing the therapeutic response of the tissue mass restenosis 11, and other tissue masses around areas 14 of the blood vessel site, to the radioactivity emitted by the radioisotope incorporated into the implantable medical device 20, e.g. stent 20, may allow the injured vessel site areas 14 beyond the length of the stent to be properly treated with radiation and thus minimize or eliminate the "candy wrapper" restenosis 11.

In order to increase the therapeutic response of the tissue mass restenosis 11 to the radioactivity emitted by the radioisotope incorporated into the implantable medical device 20, e.g. stent 20, the method of this invention employs a radiosensitizer agent 13 that is delivered at site 12 of the vessel 10 containing the radioactive implantable medical device 20, e.g. stent 20. Generally, a radiosensitizer agent is made of a large number of molecules having a metal core. When the radiosensitizer agent is delivered to the site of the injured vessel, its molecules will seek the plaque or restenosis and then proceed to bind to it as well as to the surrounding vessel wall lesion areas. Typically, most of the radiosensitizer agent molecules will accumulate in the area of the injured vessel area. When exposed to light, the radiosensitizer agent 13 increases or amplifies the therapeutic response of the tissue mass 11 to the radioactivity emitted by the radioisotope contained by the implantable medical device 20, e.g. radioactive stent 20. In effect, the radiosensitizer agent 13 acts in such manner so as to extend the range of the radiation dose beyond the physical length 21 of the implantable medical device 20, e.g. stent 20, to treat the entire injured blood vessel area 12, including areas 14 that may contain the "candy wrapper" restenosis 11.

Figure 2:
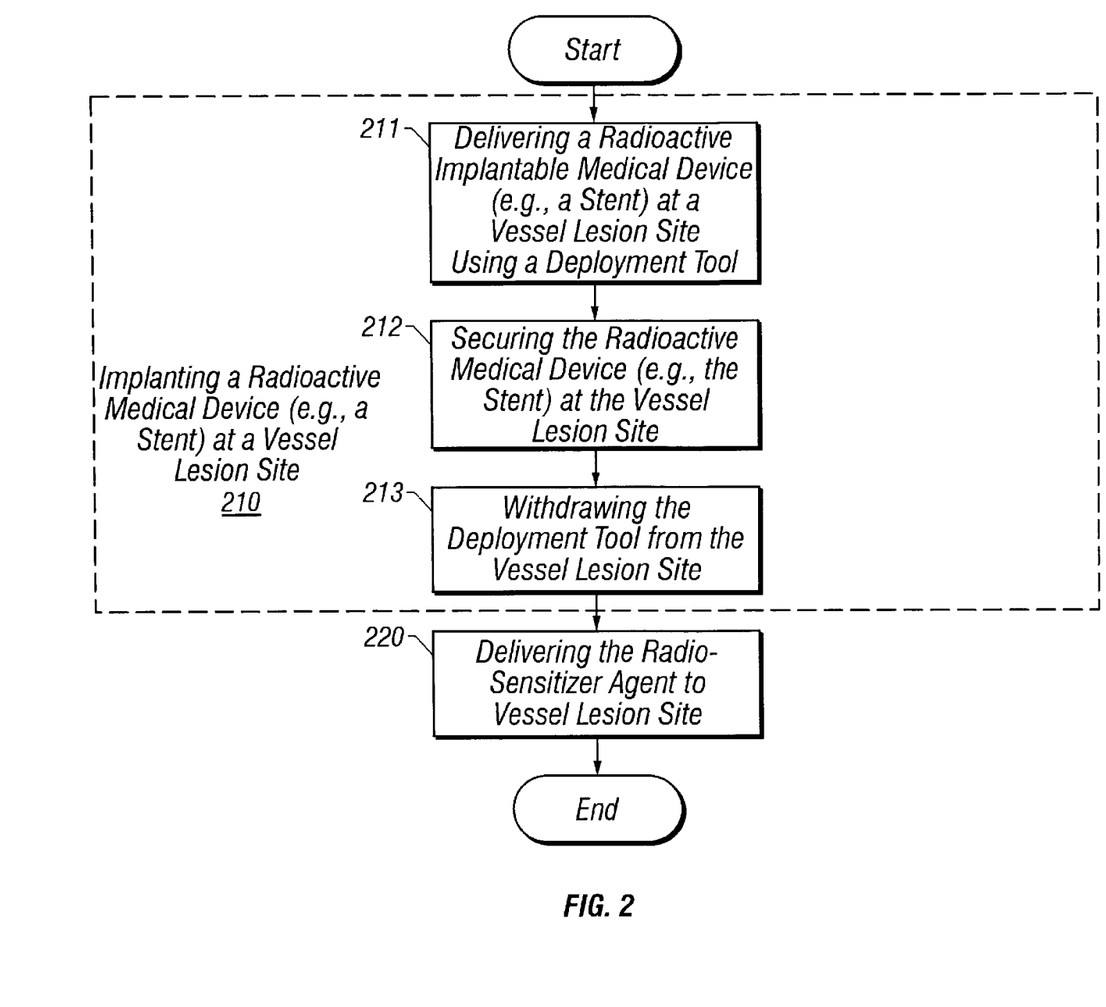
FIG. 2 is a flow chart illustrating an embodiment of a process for radiation therapy for inhibition of vascular restenosis using an intravascular radioactive implantable device and a radiosensitizer agent.

FIG. 2 illustrates an embodiment of a process for radiation therapy for inhibition of vascular restenosis using an intravascular radioactive implantable device, such as a stent, and a radiosensitizer agent. In an embodiment, the method may begin by implanting a radioactive medical device, such as a stent, at the vessel lesion site using a deployment tool (shown as step 210 in FIG. 2). Once the radioactive medical device, e.g., stent, is properly positioned and deployed, a radiosensitizer agent is delivered at the site of the injured vessel (shown as step 220 in FIG. 2). As stated above, the role of the radiosensitizer agent is increase or amplify the therapeutic response of the tissue mass to the radioactivity emitted by the radioisotope contained by the implantable medical device such that the entire injured blood vessel area, including the "candy-wrapper" restenosis, is treated by radiation.

It should be noted that the method of this invention may also be practiced by reversing the order of steps 210 and 220 discussed above. For example, the method of this invention may start by delivering a radiosensitizer agent to the injured vessel area (step 220 in FIG. 2), followed by implanting a radioactive stent at the vessel lesion site (step 210 in FIG. 2). In one embodiment, the method of this invention may be practiced by performing steps 210 and 220 of FIG. 2 substantially concurrently. In this embodiment, implanting a medical device (step 210) and delivering a sensitizing agent (step 220) to the injured vessel area are performed at substantially the same time. The following paragraphs provide a detailed discussion of each of the above two actions of the method of this invention.

It will be noted that the frequency of delivering a radiosensitizer agent to the injured vessel area (step 220 in FIG. 2) is not limited to a one time only application and may vary to include several approaches. In one configuration, delivering a radiosensitizer agent to the injured vessel area (step 220 in FIG. 2) may be performed as a one time only application. In another configuration, delivering a radiosensitizer agent to the injured vessel area (step 220 in FIG. 2) may be performed in multiple applications, either within a short period of time from the start of the patient treatment or over a more extended treatment time period, i.e., several months, from the start of patient treatment. The frequency of delivering a radiosensitizer agent to the injured vessel area may depend on a number of factors, including but not limited to the medical condition of the patient, the stage or growth of the restenosis, the type of radiosensitizing agent used, etc.

Implanting Radioactive Medical Device at Injured Vessel Site

With reference to FIG. 2, implanting a radioactive medical device, such as a stent, to the vessel lesion site is generally performed using a deployment tool. In one embodiment, if a stent is used as the implantable medical device, the stent may generally be deployed using a catheter. It will be noted, however, that other types of deployment devices may also be used within the scope of the invention described herein.

If a stent is used as the implantable medical device, the stent is generally transported in its non-expanded (i.e., delivery) diameter through the patient's vasculature until the stent reaches the injured vessel site. Typically, the stent is attached onto the catheter itself or onto another device, which is then attached to or disposed within the catheter.

In one embodiment, if the stent is not a self-expanding stent, the catheter may include an inflatable balloon or a spring-like device positioned at a distal section of the catheter. The non self-expanding stent is generally positioned over the inflatable balloon or spring-like device of the catheter. In another embodiment, the stent may be a self-expanding type stent, which typically would not require a balloon or like device in order to reach its full expanded diameter configuration. Instead, a self-expanding stent embodiment would be kept in non-expanded configuration using a sheath or like device.

Continuing with reference to FIG. 2 (step 211) the catheter-stent assembly may then be inserted into a patient's vasculature area and the stent is transported to the treatment site. Generally, a guide wire is disposed along the vascular portion where the treatment site is located. The catheter-stent assembly may be advanced over the guide wire until the length of stent is substantially centered within the blood vessel or other vascular site. Depending on the stent assembly used, a delivery sleeve may have to be retracted in order to prepare the stent to be radially expanded to an expanded diameter.

Continuing with reference to FIG. 2 (step 212), once the stent has been delivered at the vessel site, the stent is generally expanded from its delivery diameter to an expanded diameter. For a non self-expanding stent configuration, if a balloon catheter is used, the stent may be expanded by inflating the balloon portion of catheter with an inflation medium, such as a saline-based solution. Other balloon inflation media also may be used to inflate the balloon portion. Typical inflation pressures for an inflation medium such as a saline-based solution may be in the range of approximately 5 to 20 atm.

Expansion of the balloon in turn expands the stent to an expanded diameter against the vessel wall. The balloon portion may include one or more balloon markers, such as a distal marker and a proximal marker. One purpose of the distal and proximal balloon markers is to provide a better indication of the stent and the balloon portion inside the vessel.

In another embodiment, at step 212, for self-expanding implantable medical devices, e.g. stents, the sheath enveloping the compressed self-expanding stent is removed or retracted, allowing the stent to self expand at the treatment site. One or more radiopaque markers may be disposed on the sheath itself or on the self-expanding stent to provide an indication of the stent position and the expanded diameter configuration inside the vessel.

Continuing with reference to FIG. 2 (step 213), following stent expansion, the balloon is deflated and the catheter assembly is withdrawn, leaving the stent in place at the vessel lesion site. It will be noted that when using a self-expanding stent, withdrawing the catheter assembly from the patient's vasculature area (step 213) may be completed without having to deflate a balloon.

Delivering a Radiosensitizer Agent to the Injured Vessel Site

With reference to FIG. 2, in one embodiment, once the radioactive stent is properly positioned and deployed at the injured vessel area, a radiosensitizer agent is delivered to the site of the injured vessel (step 220 in FIG. 2). In one embodiment, the radiosensitizer agent may be delivered to the site of the vessel using an injection technique, such as intravenous (IV) injection, or any other injection-type technique such as injection catheters. In another embodiment, the radiosensitizer agent may be locally delivered to the vessel site using a catheter or a similar device, such as a microporous balloon. Alternatively, the radiosensitizer agent may be locally delivered to the vessel site using the implantable medical device, e.g. stent, itself For example, the radiosensitizer agent may be coated onto the implantable medical device, e.g. stent, or coated onto a portion of the deployment tool, such as the balloon.

The radiosensitizer agent will typically bind to the diseased tissue area by binding to either lipid-rich cells or macrophages/monocytes. The radiosensitizer agent may be activated by the radiation emitted from the intravascular radiation stent or by a laser (not shown).

When exposed to radiation or laser light, the radiosensitizer agent will enhance and/or amplify the effects of radiation therapy and provide the dosimetry which the radioactive stent implant could not provide by itself. Unexposed to radiation or laser light, the radiosensitizer agent will be eliminated from the patient's body within a short period of time. For example, some radiosensitizer agents are eliminated from the body within about 17 hours.

Generally, a radiosensitizer agent is made of a large number of molecules having a metal core. When the radiosensitizer agent is delivered to the site of the injured vessel, its molecules will seek the plaque or restenosis and then proceed to bind to it as well as to the surrounding vessel wall lesion areas. Typically, most of the radiosensitizer agent molecules will accumulate in the area of the injured vessel area. When activated by radiation or laser light, the radiosensitizer agent molecules and their metal cores will be excited to a higher electronic state, causing the metal cores to increase or amplify the therapeutic response of the tissue mass to the radioactivity emitted by the radioisotope in the implantable medical device, e.g. stent. In effect, the radiosensitizer agent acts to extend the therapeutic response of the tissue mass located beyond the physical length of the implantable medical device, e.g. stent, such that the entire injured blood vessel area, including the "candy-wrapper" restenosis areas, is treated by the radioactivity emitted by the radioactive implantable medical device.

The method of this invention may be practiced using any radiosensitizer agents in the field, such as Antrin, a DNA-ligand, etc. Depending on the type of radiosensitizer agent used, the therapeutic response of the tissue mass to the radioactivity may be in a range of approximately 1 to 10. When used with a beta-emitting radioisotope, the radiosensitizer agent may extend the effective therapeutic response approximately 1 to 5 mm beyond the length of the stent. This increase in effective therapeutic response is generally sufficient to prevent or reduce most "candy wrapper" restenosis.

When used with a low energy gamma-emitting radioisotope stent, the radiosensitizer agent may extend the effective therapeutic radiation approximately 1 to 10 mm beyond the length of the stent.

To prevent or eliminate follow-up restenosis growth, the radiosensitizer agent may be administered to the injured vessel site area at regular time intervals following stent implantation and the initial treatment with the radiosensitizer agent. These time intervals may range from 1 week to 6 months following initial treatment.

Radioactive Implantable Medical Device and Deployment Tool

Figure 3:
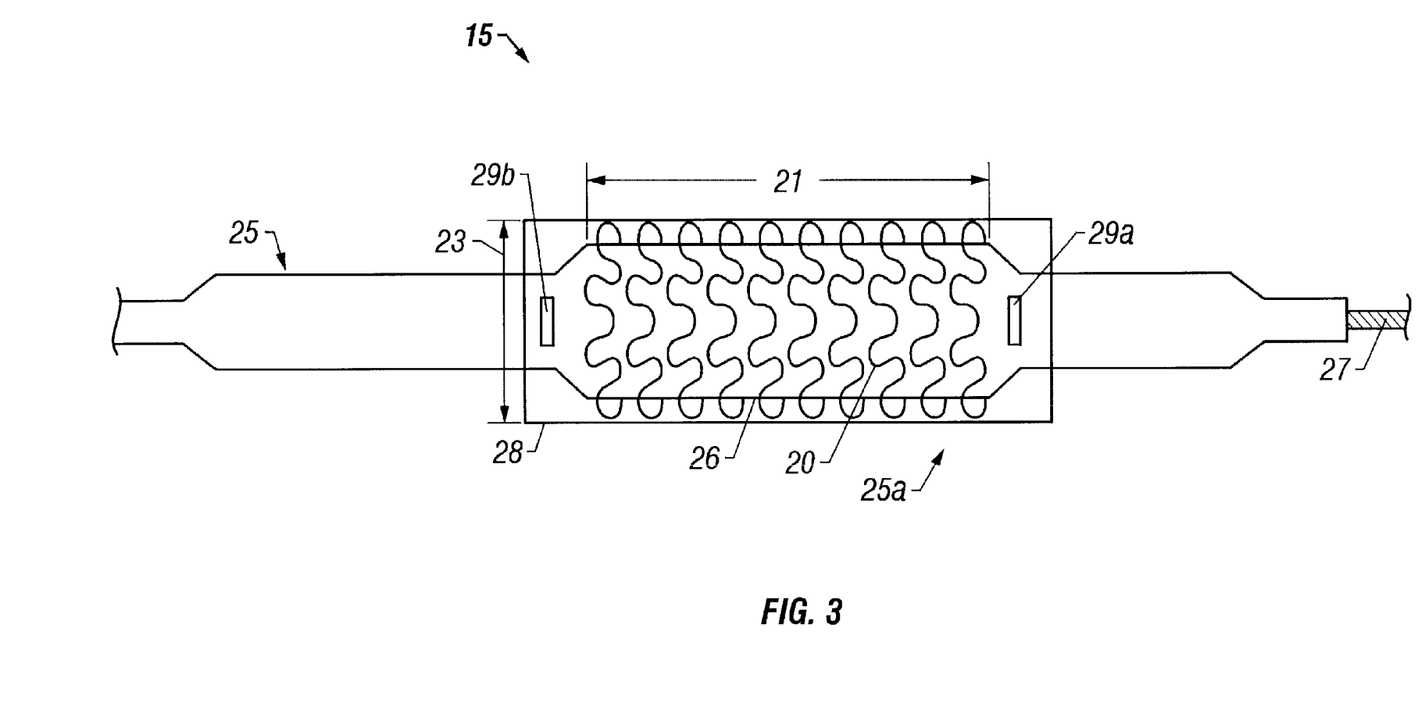
FIG. 3 illustrates an embodiment of a deployment tool for delivery and implantation of a radioactive medical device, for example a stent, at a body vessel site where "candy wrapper" effects may occur after the implantable medical device has been implanted.

FIG. 3 illustrates an embodiment of a deployment tool 25 for delivery and implantation of a non self-expanding radioactive medical device, for example a stent 20, at a body vessel site where "candy wrapper" effects may occur after the stent has been implanted.

The implantable stent 20 may be made of a metal or metal alloy (e.g., titanium, 316L stainless steel), a non-metal material (e.g., polymer-type, ceramic), or a combination thereof. If multiple stents are used, the stents typically are made of similar compositions.

Stents used for coronary applications typically have a length 21 in a range of approximately 5 to 40 mm. When deployed in their expanded configuration, coronary stents typically have an expanded diameter 23 in the range of approximately 2 to 5 mm while peripheral stents typically have an expanded diameter 23 in the range of approximately 5 to 10 mm. Generally, when used for vascular radiotherapy, the implantable stent 20 is made radioactive prior to being inserted into the patient vessel 10. The methods of this invention, however, may be practiced using a stent that is made radioactive following implantation into the patient.

Low-intensity implantable radioactive stents generally employ beta-emitting or low energy gamma-emitting radioisotopes. A beta-emitter radioisotope, such as phosphorus-32 ($P^{32}$), having a low-energy, short half-life beta particle is desired for optimum therapeutic treatment with maximum patient safety. Other beta-emitting and low-penetration gamma-emitting radioisotopes that may be used include, but are not limited to, $Sn^{123}$, $Sr^{89}$, $P^{33}$, $Pd^{103}$, $Y^{90}$, $Ru^{106}$ and $I^{125}$.

The stent may be made radioactive using various techniques. For example, the beta-emitting or gamma-emitting radioisotope may be implanted or coated on the surface of the stent. The radioisotope may also be alloyed into the metal from which the stent is made. Furthermore, the stent may be made radioactive through activation in a nuclear reactor or similar facility. Lastly, if a non-radioactive stent is implanted into patient, the stent may be made radioactive by placing a radioisotope inside the stent.

Continuing with reference to FIG. 3, in one embodiment, implanting a radioactive medical device, such as a stent 20 to the vessel lesion site is performed using a stent deployment tool 25, such a catheter 25. Catheter 25 may include an inflatable member, such as balloon 26. Generally, stent 20 may be transported in its non-extended (i.e., delivery) diameter 23 through the patient's vasculature until the stent 20 reaches the injured vessel site. The stent 20 may be attached to a distal end 25a of the catheter 25. The stent 20 is generally positioned over the inflatable balloon 26 portion of the catheter.

When disposed over or attached to catheter 25, the stent 20 and catheter 25 form assembly 15. During deployment, the catheter-stent assembly 15 is inserted into a patient's vasculature area to allow stent 20 to be transported to the treatment site. Generally, a guide wire 27 is disposed along the vascular portion where the treatment site is located. The catheter-stent assembly 15 may be advanced over the guide wire 27 until the length 21 of stent 20 is substantially centered within the blood vessel (or other vascular) site. Depending on the balloon and stent assembly used, a delivery sleeve 28 may have to be retracted in order to prepare the stent 20 to be radially expanded to an extended diameter.

Continuing with reference to FIG. 3, balloon 26 may include one or more balloon markers, such as a distal marker 29a and a proximal marker 29b, to provide a better indication of the stent 20 and the balloon 26 inside the vessel. Distal and proximal balloon markers 29a and 29b may include radiopaque markers made of any materials, such as silver, gold, platinum, tungsten, or others that allow markers to be visible under a fluoroscope. In one embodiment, the radiopaque markers are attached to the balloon itself.

Figure 4:
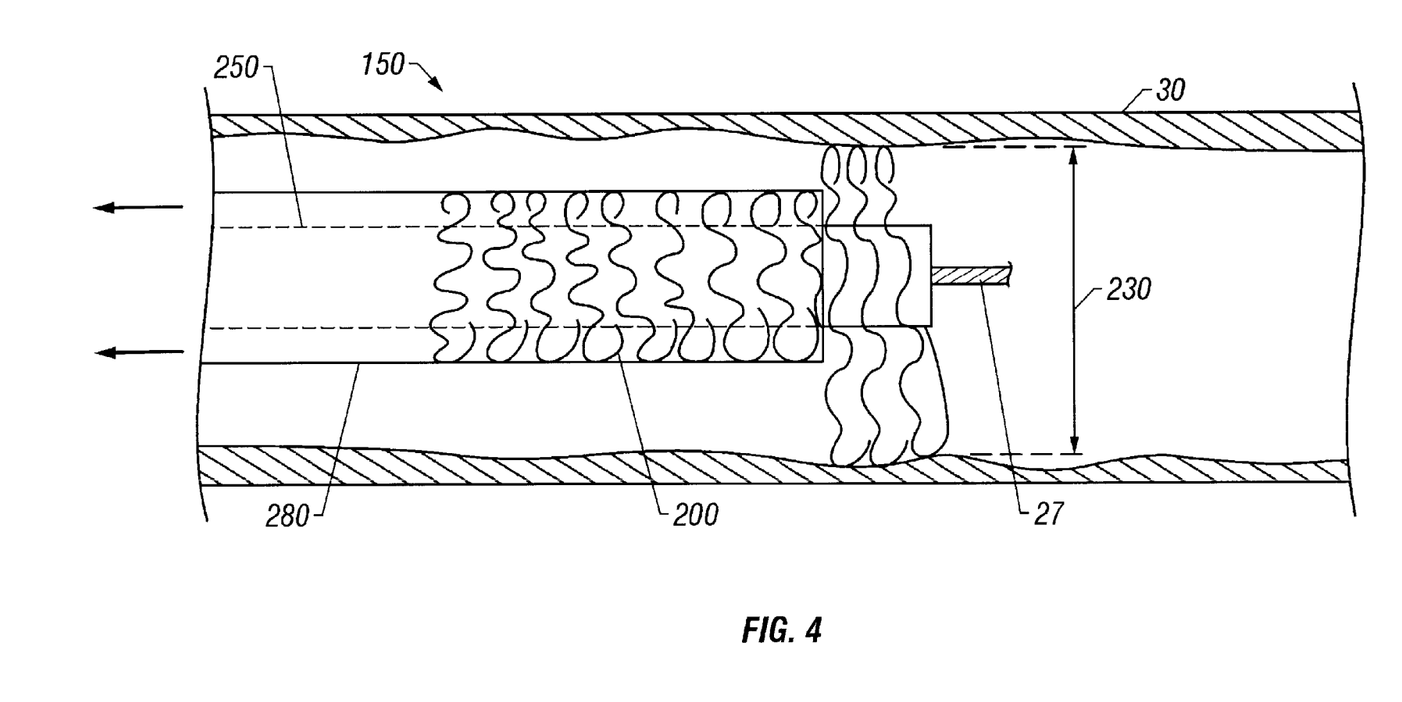
FIG. 4 illustrates another embodiment of a deployment tool for delivery and implantation of a radioactive medical device, for example a stent, at a body vessel site where "candy wrapper" effects may occur after the implantable medical device has been implanted.

Turning now to FIG. 4, another embodiment of a deployment tool 250 for delivery and implantation of a self-expanding radioactive medical device 200, for example a self-expanding stent 200, is illustrated.

The implantable self-expanding stent 200 may be made of a metal or metal alloy (e.g., titanium, 316L stainless steel), a non-metal material (e.g., polymer-type, ceramic), or a combination thereof. If multiple self-expanding stents are used, the stents typically are made of similar compositions.

As with the non self-expanding stent configurations, self-expanding stents used for coronary applications typically have a length in a range of approximately 5 to 30 mm. When deployed in their expanded configuration, coronary stents typically have an expanded diameter in the range of approximately 2 to 5 mm while peripheral stents typically have an expanded diameter in the range of approximately 5 to 10 mm.

Generally, when used for vascular radiotherapy, the implantable self-expanding stent 200 is made radioactive prior to being inserted into the patient vessel. The methods of this invention, however, may be practiced using a stent that is made radioactive following implantation into the patient.

Low-intensity implantable self-expanding radioactive stents generally employ beta-emitting or low energy gamma-emitting radioisotopes. A beta-emitter radioisotope, such as phosphorus-32 ($P^{32}$), having a low-energy, short half-life beta particle is desired for optimum therapeutic treatment with maximum patient safety. Other beta-emitting and low-penetration gamma-emitting radioisotopes that may be used include, but are not limited to, $Sn^{123}$, $Sr^{89}$, $P^{33}$, $Pd^{103}$, $Y^{90}$, $Ru^{106}$ and $I^{125}$.

The stent may be made radioactive using various techniques. For example, the beta-emitting or gamma-emitting radioisotope may be implanted or coated on the surface of the stent. The radioisotope may also be alloyed into the metal from which the stent is made. Furthermore, the stent may be made radioactive through activation in a nuclear reactor or similar facility. Lastly, if a non-radioactive stent is implanted into patient, the stent may be made radioactive by placing a radioisotope inside the stent.

Continuing with reference to FIG. 4, in one embodiment, implanting a self-expanding radioactive medical device, such as a self-expanding stent 200 to the vessel lesion site is performed using a stent deployment tool 250, such a catheter 250. Catheter 250 generally includes a sheath 280 or like device whose purpose is to keep the self-expanding stent 250 in non-expanded configuration.

Generally, the self-expanding stent 200 is transported in its non-expanded (i.e., delivery) diameter through the patient's vasculature 30 until the stent 200 reaches the injured vessel site. The self-expanding stent 200 may be attached to a distal end of the catheter 250. When disposed over or attached to catheter 250, the stent 200 and catheter 250 form assembly 150. During deployment, the catheter-stent assembly 150 is inserted into a patient's vasculature area to allow stent 200 to be transported to the treatment site. Generally, a guide wire 27 is disposed along the vascular portion where the treatment site is located. The catheter-stent assembly 150 may be advanced over the guide wire 27 until the length of stent 200 is substantially centered within the blood vessel (or other vascular) site. Once positioned at the desired blood vessel site, the sheath 280 is retracted to enable the self-expanding stent 200 to radially self-expand itself to an extended diameter 230 against the vessel walls.

A method and apparatus for inhibition of vascular restenosis using an intravascular radioactive implant device and a radiosensitizer agent have been described. Although specific embodiments, including specific parameters, methods, and materials have been described, various modifications to the disclosed embodiments will be apparent to one of ordinary skill in the art upon reading this disclosure. Therefore, it is to be understood that the embodiments described above are merely illustrative of and not restrictive on the broad invention and that this invention is not limited to the specific embodiments shown and described.

I claim:

1. A method comprising:
   implanting a medical device at a blood vessel site that has undergone a procedure to open a stenosed region within a blood vessel, the medical device comprising a radioisotope to emit a radioactivity to a tissue mass at the blood vessel site; and
   delivering a radiosensitizer agent to the tissue mass at the blood vessel site, the radiosensitizer agent increasing a therapeutic response of the tissue mass to the radioactivity emitted by the radioisotope by extending a range of a radiation dose beyond a length of the medical device.

2. The method of claim 1, wherein implanting the medical device at the blood vessel site comprises:
   inserting the medical device into the blood vessel using a deployment tool;
   advancing the medical device to the blood vessel site using the deployment tool;
   securing the medical device at the blood vessel site; and
   withdrawing the deployment tool from the blood vessel.

3. The method of claim 2 further comprises positioning the medical device at the blood vessel site using the deployment tool to center the medical device within the blood vessel site.

4. The method of claim 2 wherein the deployment tool is a balloon catheter comprising an inflatable balloon disposed at a distal end of a catheter shaft.

5. The method of claim 1 wherein the radioisotope comprises a beta-emitting radioisotope.

6. The method of claim 1 wherein the radioisotope comprises a gamma-emitting radioisotope.

7. The method of claim 1 wherein delivering the radiosensitizer agent to the blood vessel site comprises injecting the radiosensitizer agent into the patient.

8. The method of claim 1 wherein delivering the radiosensitizer agent to the blood vessel site comprises using a catheter positioned proximate to the blood vessel site.

9. The method of claim 1 wherein delivering the radiosensitizer agent to the blood vessel site comprises using the medical device implanted at the blood vessel site.

10. The method of claim 1 wherein the radiosensitizer agent comprises a DNA-ligand.

11. The method of claim 1 wherein the radiosensitizer agent comprises Antrin.

12. The method of claim 1 wherein the therapeutic response of the tissue mass increases by a factor in the range of approximately 1 to 10.

13. A method for inhibiting restenosis, the method comprising:
   implanting a stent at a blood vessel site which has undergone a procedure to open a stenosed region within a blood vessel, the stent comprising a radioisotope to emit a radioactivity to a tissue mass at the blood vessel site; and
   delivering a radiosensitizer agent to the tissue mass at the blood vessel site, the radiosensitizer agent increasing a therapeutic response of the tissue mass to the radioactivity emitted by the radioisotope by extending a range of a radiation dose beyond a length of the medical device.

14. The method of claim 13 wherein implanting the stent at the blood vessel site comprises:
   inserting the stent into the blood vessel using a stent deployment tool;
   advancing the stent to the blood vessel site using the stent deployment tool;
   radially expanding the stent at the blood vessel site until the stent reaches an expanded stent diameter; and
   withdrawing the stent deployment tool from the blood vessel.

15. The method of claim 14 further comprises positioning the stent at the blood vessel site using the stent deployment tool to center the stent within the blood vessel site.

16. The method of claim 14 wherein the stent deployment tool is a balloon catheter comprising an inflatable balloon disposed at a distal end of a catheter shaft.

17. The method of claim 16 wherein the stent is positioned over the inflatable balloon.

18. The method of claim 17 wherein radially expanding the stent includes pressurizing the inflatable balloon with an inflatable medium.

19. The method of claim 18 wherein withdrawing the balloon catheter assembly comprises:

deflating the inflatable balloon by withdrawing the inflation medium from the inflatable balloon; and withdrawing the balloon catheter from the blood vessel.

20. The method of claim 16 wherein the inflatable balloon includes at least one marker to provide an indication of the expanded stent diameter.

21. The method of claim 14 wherein advancing the stent to the blood vessel site includes advancing the stent over a guide wire disposed along the blood vessel site.

22. The method of claim 14 wherein the stent comprises a self-expanding stent.

23. The method of claim 22 wherein radially expanding the stent includes retracting a delivery sleeve disposed over the stent.

24. The method of claim 14 wherein the expanded stent diameter is in the range of approximately 2 to 5 mm.

25. The method of claim 13 wherein the stent has a length in the range of approximately 5 to 40 mm.

26. The method of claim 13 wherein the radioisotope comprises a beta-emitting radioisotope.

27. The method of claim 13 wherein the radioisotope comprises a gamma-emitting radioisotope.

28. The method of claim 13 wherein delivering the radiosensitizer agent to the blood vessel site comprises injecting the radiosensitizer agent into the patient.

29. The method of claim 13 wherein delivering the radiosensitizer agent to the blood vessel site comprises using a catheter positioned proximate to the blood vessel site.

30. The method of claim 13 wherein delivering the radiosensitizer agent to the blood vessel site comprises using the stent.

31. The method of claim 13 wherein the radiosensitizer agent comprises a DNA-ligand.

32. The method of claim 13 wherein the radiosensitizer agent comprises Antrin.

33. The method of claim 13 wherein the therapeutic response of the tissue mass increases by a factor in the range of approximately 1 to 10.

34. The method of claim 13 further comprising activating the radiosensitizer agent using a laser beam.

35. The method of claim 13 wherein the radiosensitizer agent is delivered prior to implanting the stent.

36. The method of claim 13 wherein implanting the stent and delivering the radiosensitizer agent are performed at substantially the same time.

37. The method of claim 13 wherein the stent is made radioactive prior to implanting the stent.

38. A radiation therapy system comprising:

an implantable medical device comprising a radioisotope to emit a radioactivity to a tissue mass at a blood vessel site which has undergone a procedure to open a stenosed region within a blood vessel; and a radiosensitizer agent that increases a therapeutic response of the tissue mass to the radioactivity emitted by the radioisotope by extending a range of a radiation dose beyond a length of the medical device, wherein the radioisotope and the radiosensitizer agent are disposed at the blood vessel site during radiation therapy.

39. The radiation therapy system of claim 38 wherein the radioisotope comprises a beta-emitting radioisotope.

40. The radiation therapy system of claim 38 wherein the radioisotope comprises a gamma-emitting radioisotope.

41. The radiation therapy system of claim 38 wherein the radiosensitizer agent is disposed at the blood vessel site by injecting the radiosensitizer agent into a patient.

42. The radiation therapy system of claim 38 wherein the radiosensitizer agent is disposed at the blood vessel site using a catheter positioned proximate to the blood vessel site.

43. The radiation therapy system of claim 38 wherein the radiosensitizer agent comprises Antrin.

44. The radiation therapy system of claim 38 wherein the therapeutic response of the tissue mass increases by a factor in the range of approximately 1 to 10.

45. A method comprising:

implanting a medical device at a blood vessel site, the medical device comprising a radioisotope to emit a radioactivity to a tissue mass at the blood vessel site; and delivering a radiosensitizer agent to the tissue mass at the blood vessel site, the radiosensitizer agent increasing a therapeutic response of the tissue mass to the radioactivity emitted by the radioisotope by extending a range of a radiation dose beyond a length of the medical device.

46. The method of claim 45, wherein implanting the medical device at the blood vessel site comprises:

inserting the medical device into the blood vessel using a deployment tool;

advancing the medical device to the blood vessel site using the deployment tool;

securing the medical device at the blood vessel site; and withdrawing the deployment tool from the blood vessel.

47. The method of claim 46 further comprises positioning the medical device at the blood vessel site using the deployment tool to center the medical device within the blood vessel site.

48. The method of claim 46 wherein the deployment tool is a balloon catheter comprising an inflatable balloon disposed at a distal end of a catheter shaft.

49. The method of claim 45 wherein the radioisotope comprises a beta-emitting radioisotope.

50. The method of claim 45 wherein the radioisotope comprises a gamma-emitting radioisotope.

51. A radiation therapy system comprising:

an implantable medical device comprising a radioisotope to emit a radioactivity to a tissue mass at a blood vessel site; and a radiosensitizer agent that increases a therapeutic response of the tissue mass to the radioactivity emitted by the radioisotope by extending a range of a radiation dose beyond a length of the medical device, wherein the radioisotope and the radiosensitizer agent are disposed at the blood vessel site during radiation therapy.

52. The radiation therapy system of claim 51 wherein the radioisotope comprises a beta-emitting radioisotope.

53. The radiation therapy system of claim 51 wherein the radioisotope comprises a gamma-emitting radioisotope.

54. The radiation therapy system of claim 51 wherein the radiosensitizer agent is disposed at the blood vessel site by injecting the radiosensitizer agent into a patient.

55. The radiation therapy system of claim 51 wherein the radiosensitizer agent is disposed at the blood vessel site using a catheter positioned proximate to the blood vessel site.

56. The radiation therapy system of claim 51 wherein the radiosensitizer agent comprises Antrin.

57. The radiation therapy system of claim 51 wherein the therapeutic response of the tissue mass increases by a factor in the range of approximately 1 to 10.

* * * * *